United States Patent [19]

Coulthard et al.

[11] Patent Number: 4,512,103
[45] Date of Patent: Apr. 23, 1985

[54] METHOD FOR PRODUCING FUNGI

[76] Inventors: T. Lionel Coulthard, R.R. #2, Ganges, B.C., Canada, V0S 1E0; Phillip M. Townsley, 4569 W. 13th Ave., Vancouver, B.C., Canada, V6R 2V5; Hugh S. Saben, 819 W. 20th Ave., Vancouver, B.C., Canada, V52 1Y3

[21] Appl. No.: 475,064

[22] Filed: Mar. 14, 1983

Related U.S. Application Data

[63] Continuation-in-part of Ser. No. 279,475, Jul. 1, 1981, abandoned, which is a continuation-in-part of Ser. No. 104,763, Dec. 18, 1979, Pat. No. 4,292,328, which is a continuation-in-part of Ser. No. 935,141, Aug. 21, 1978, abandoned, which is a continuation of Ser. No. 679,994, Apr. 26, 1976, abandoned.

[51] Int. Cl.³ .............................................. A01G 1/04
[52] U.S. Cl. .............................................. 47/1.1; 71/5
[58] Field of Search .................................. 47/1.1; 71/5

[56] References Cited

U.S. PATENT DOCUMENTS

| | | | |
|---|---|---|---|
| 2,928,210 | 3/1960 | Cirillo et al. | 47/1.1 |
| 3,286,399 | 11/1966 | Laniece | 47/1.1 |
| 3,942,969 | 3/1976 | Carroll et al. | 47/1.1 X |
| 3,996,038 | 12/1976 | Toth et al. | 47/1.1 X |
| 4,127,964 | 12/1978 | Mee | 47/1 |
| 4,292,328 | 9/1981 | Coulthard et al. | 426/2 |

OTHER PUBLICATIONS

Pure Cultural . . . , Townsley, Ann. Mtg. Fraser Valley Mushroom Growers Corp. Assoc. 1973.
Biological Control . . . , Tautorus et al., Appl. & Environmental Microbiol. 1983, pp. 511–515.

Primary Examiner—Robert E. Bagwill
Attorney, Agent, or Firm—Christensen, O'Connor, Johnson & Kindness

[57] ABSTRACT

Nutrients for supporting fungi growth, and particularly mushroom growth, are provided by a liquid nutrient comprising the product of a thermophilic digestion process. The liquid nutrient is contacted with and absorbed in a support medium to form a growing bed. The liquid nutrient is inoculated with spawn of the particular fungi to be grown. The inoculated product is then maintained under temperature and humidity conditions that promote mycelia growth. Once mycelia appear, the growing bed can be cased to promote the growth of fruiting bodies. The growing bed can be replaced on a batch basis. Alternatively, the bed can be irrigated on an intermittent or continuous basis to replenish the nutrient supply.

9 Claims, No Drawings

METHOD FOR PRODUCING FUNGI

BACKGROUND OF THE INVENTION

This application is a continuation-in-part of prior copending application Ser. No. 279,475, filed July 1, 1981 (now abandoned), which is in turn a continuation-in-part of prior copending application Ser. No. 104,763, filed Dec. 18, 1979 (now U.S. Pat. No. 4,292,328), which in turn is a continuation-in-part of prior copending application Ser. No. 935,141, filed Aug. 21, 1978 (now abandoned), which in turn is a continuation of prior application Ser. No. 679,994, filed Apr. 26, 1976 (now abandoned), the benefit of the filing dates of which are hereby claimed under 35 USC 120.

The present invention relates to the production of fungi, and more particularly to the production of edible mushrooms on a commerical scale.

Fungi, and particularly commercial mushrooms of the genus *Agaricus,* and more particularly *Agaricus bisporus,* are important food and agricultural crops in the western parts of the North American continent. In some areas it ranks second only to the potato in economic importance as a vegetable crop. Not only has the mushroom gained acceptance in numerous food preparations, but also there is substantial evidence to indicate that the mushroom has considerable nutritional value.

The methods employed to commerically grow mushrooms have not changed significantly over the years. Conventionally, the mushroom is grown on composted plant material containing animal manures as a nutrient and a microbial inoculum. In order to successfully grow mushroom cultures on such compost beds, the compost must reach a final compost temperature of between 50° and 65° C. Composting at these temperatures is commonly referred to as either "pasteurizing" or "sweating-out." Composts that either have not attained these temperatures or have exceeded them will not likely yield an economic mushroom crop.

Significant problems are encountered in achieving the sweating-out period under natural composting conditions. Thus, the growing beds comprised of such composting materials must be carefully checked to assure that no undesirable bacteria or other microflora that can affect the mushroom output have entered the bed. The inability to accurately control the sweating-out temperatures and/or the migration of unwanted microflora into the composting beds can result in the loss of mushroom crops and thus economic damage to the grower.

It is a broad object of the present invention to provide a physical support for growing mushrooms into which is incorporated, at the intiation of a mushroom growing cycle, a liquid processed by thermophilic digestion. It is furthermore an object of the present invention to provide a fungi growing bed with quality nutrient material containing microflora developed to support fungal growth on either a batch or continuous basis. A further object of the present invention is to provide nutrients for a fungi growing bed that do not require conventional composting of solids and the attendant labor and control which must be exercised in connection with the conventional composting of solids and preparation of animal materials for use as a growth-supporting medium. It is a further object of the present invention to provide a mushroom growing bed for which neither the liquid nutrient nor the physical support medium need be sterilized. It is a further object of the present invention to provide an economic and efficient method for producing fungi and especially for producing edible mushrooms on a commerical scale.

SUMMARY OF THE INVENTION

The foregoing objects, and other objects that will become apparent to one of ordinary skill after reading the ensuing specification are provided by the method of the present invention for producing fungi. A relatively inert support medium for physically supporting fungi growth is first provided. The support medium is contacted with a liquid nutrient comprising the product of a thermophilic digestion of a biodegradable organic material. The combination of the physical support medium and the liquid nutrient provide a growing bed for supporting the growth of fungi. The support medium containing the liquid nutrient is then inoculated with spawn. The growing bed containing the liquid product is then maintained at a predetermined temperature and moisture content to promote the growth of mycelia. If fruiting bodies are desired as an end product, the bed is then cased with appropriate material. Again, the cased bed is maintained at predetermined temperature and moisture conditions which will promote the growth of fruiting bodies. Once the fruiting bodies reach an appropriate size, they can be harvested.

DETAILED DESCRIPTION OF THE INVENTION

Fungi production in accordance with the present invention can be conducted on a batch or continuous basis. If conducted on a batch basis, a liquid nutrient product produced by a thermophilic digestion process, which will be more completely discussed below, is contacted with a preferably absorbent or adsorbent substrate or support medium. Solid material from the same thermophilic digestion process can also be used by placing it in a composting bin and later using it as a nutrient for supporting fungi growth. In any event, the support medium is preferably saturated with the nutrient liquid from the thermophilic digestion process. The medium saturated support is then spread into growing beds of appropriate thickness, usually on the order of two to seven inches. The growing bed can then be inoculated with spawn of the desired fungi.

Once inoculated, a growing bed is maintained under a controlled environment in which temperature and humidity are closely monitored and controlled to optimize the growing conditions for the particular fungi being produced. After a few days, mycelia appear in the bed. The mycelia can be harvested if they are particularly useful. However, if, for example, edible mushrooms are to be grown, the growing bed is cased with a casing material conventionally used in growing mushrooms. The casing material normally used is a mixture of sphagnum moss and calcium carbonate (limestone). The casing is placed over the basic growing bed over a depth of 0.5 to 1.5 inches, preferably on the order of about 0.75 to 1.0 inches. The casing material promotes the growth of mushroom fruiting bodies. After the casing step has been completed, the cased beds are again maintained in an environment where the temperature and humidity are very closely monitored and controlled to optimize the growing condition for the fruiting bodies. After a few days, the fruiting bodies appear as "pinheads" at or near the top surface of the casing material and within approximately ten days thereafter can normally be commercially harvested.

In a batchwise process, sometimes two to four crops, called "flushes" can be obtained before the nutrient value of the liquid nutrient from the thermophilic digestion process is substantially exhausted. If desired, fungi production, and especially mushroom production, can also be accomplished on a continuous basis. The beds can be designed so that once a substantial portion of the nutrient value of the liquid nutrient in a particular growing bed has been consumed, additional liquid nutrient can be supplied by subirrigation of the bed to resaturate the support medium with liquid nutrient having adequate nutrient value to support fungi growth. In this manner, after two or three crops of mushrooms have been harvested, the growing bed can be subirrigated so as to replenish the nutrient supply.

The support medium used in conjuction with the present invention is unique in that it can be comprised of a relatively inert material such as brick fragments, wood chips, sponge, or any other non-pathogenic, inert material that can absorb or adsorb and retain sufficient amounts of liquid nutrient and provide support for the mushroom fruiting body and casing materials. Absorbent materials such as brick fragments and wood chips can be saturated with the liquid nutrient by merely immersing the support medium in the liquid nutrient or by spraying the liquid nutrient over the support medium. The liquid nutrient can be sprayed at digestion temperatures over the support medium, or can first be cooled and then sprayed over the support medium. Additionally, there is also a residue or solid product that results from the thermophilic digestion process described in more detail below. This solid product has a relatively high water content (on the order of 65% to 75% by weight) and can itself be utilized as a support bed for growing mushroom fruiting bodies.

One digestion process for producing a liquid nutrient is described in complete detail in prior copending application Ser. No. 104,763, filed Dec. 18, 1979, now U.S. Pat. No. 4,292,328, expressly incorporated by reference herein. The digestion process is an aerobic thermophilic process that can achieve thermophilic digestion temperatures of on the order of 50° C. to 85° C. Aqueous nutrient liquid product for use in accordance with the present invention can be produced by thermophilic digestion of a broad spectrum of biodegradable organic materials, for example, carbonaceous solid wastes such as human wastes, including sewage sludges, carbonaceous domestic and industrial wastes such as fruit and vegetable processing wastes, animal packing plant waste, fish cannery waste, lignocellulosic, cellulosic and other woody materials. Other materials such as garbage wastes, for example, fruit and vegetable peels, chicken feathers, and the like can also be thermophilically digested to produce liquid nutrient.

Thermophilic digestion temperatures can be achieved with biodegradable organic material without the addition of external heat to the digesting system. Preferably, the digesting vessel, or digester, in which the material is being digested is sufficiently insulated to prevent any substantial amount of heat loss through the walls and the bottom of the digester. The top of the digester can be left open to the atmosphere but is essentially insulated by an aerated foam-like layer of material that develops during the digestion process. When the digesting material is properly aerated and agitated, digestion will occur so that a proper succession of microorganisms will be developed. It is important that the aeration rates and agitation rates be such that no anaerobic regions develop within the digesting mass. These microorganisms are thermogenic and are favored in a temperature range between about 50° C. and 85° C.

The biodegradable material is normally in an aqueous medium. If necessary, water is added to the material to enable thorough mixing of the slurry and to render it easily agitatable. Typically, if the dry solids content of the aqueous biodegradable mixture is on the order of about five percent by weight to about ten percent by weight of the total aqueous mixture in the digester when the process is initiated, thermophilic temperatures can be achieved without the addition of external heat. However, for purposes of the present invention, it is satisfactory to supply heat to the digester if necessary, especially if ambient conditions are very cold, to assist raising the temperature of the digesting mass to the thermophilic range. Furthermore, heat can be added to the digesting mass to maintain the temperature within the thermophilic temperature range for a required period of time. Normally, after the digesting mass has been maintained within the thermophilic temperature range for on the order of 0.5 to four days, the liquid product, and in fact the residue or solid product that settles to the bottom of the digester, are ready to be employed in their role as a nutrient source for growing fungi in accordance with the present invention.

Oxygenation is required to raise the temperature of the digesting mass to the thermophilic temperature range and maintain it for a prescribed period of time within that range. Oxygenation rates must be maintained sufficiently high so that the dissolved oxygen content prior to achieving thermophilic digestion temperatures will be on the order of 0.1 to 0.2 mg/l. Once thermophilic digestion temperatures have been achieved, the dissolved oxygen level should be maintained at on the order of 0.5 mg/l. or higher. It is also important that the oxygenating gas such as air be introduced adjacent the bottom of the digesting vessel. It is also important that the agitator, normally an impeller, be positioned adjacent the bottom of the digesting tank, but above the sparger or other device utilized to introduce the air into the slurry in the tank.

Once the liquid nutrient has been withdrawn from the digester, and cooled, it can be inoculated with fungi spawn. The inoculation can take place either prior to or subsequent to the saturation of the support medium with the nutrient liquid. Although fungi of many types can be grown in accordance with the present invention, for example, those from the genus Pleurotus, it is presently preferred that edible mushrooms from the genus Agaricus, and specifically *Agaricus bisporus,* be employed. Once the spawn has been distributed over the growing bed, comprising the liquid nutrient and medium, the growing environment in which the growing bed is located can be closely regulated. Normally, the temperature and humidity in the growing rooms are maintained to optimize the growing conditions for the particular fungi being grown. For the *A. bisporus,* the temperature can be maintained in the range of from 24° C. to 33° C. and preferably from 24° C. to 26° C. while the humidity is maintained close to saturation conditions. The growing beds must also be moistened periodically to assure that the bed moisture content does not drop below approximately 62% by weight. After a few days in the controlled environment, mycelia are generated from the spawn. Once the mycelia have grown to a sufficient density the mycelia can be harvested. Mycelia can be grown in this manner, for example, for use in the pulp and paper industry and as animal feed.

If, however, mushrooms are to be grown, the growing bed is "cased" with a casing material when the mycelia have appeared throughout the bed. Normally, this casing material comprises a mixture of calcium carbonate and sphagnum moss or other conventional material that will support fruiting mushroom bodies. The water-moistened material is normally placed on the growing bed to a depth of 0.75 to 1.0 inches. The cased beds are then again maintained at preferred temperatures on the order of 13° to 16° C. and a relative humidity of on the order of 88 to 94 percent with air movement provided. Fruiting bodies will normally appear within about ten days.

It is most preferred that the liquid nutrient from the thermophilic digestion process be combined with a support medium in the ratio of about 64 milliliters of liquid to about 36 g (dry weight) of support medium, to produce a growing bed having about 64% liquid. A liquid nutrient concentration in the growing beds on this order will support, for example, three or four crops of mushrooms before the bed must be replaced or before subirrigation for a continuous growing bed must be repeated. It is also to be understood that various additional nutrients needed by the mushrooms and not produced by the thermophilic digestion can be added to the liquid nutrient as the original digestible material is being digested or before the liquid nutrient is combined with the support medium. It is also recognized that certain bacteria developed in the liquid nutrient produced by the thermophilic digestion process described above will provide a nutrient more favorable for mushroom growth than other prior materials.

EXAMPLE

The following example is intended to illustrate to one of ordinary skill in the art of growing mushrooms how to use the present invention. It is not intended in any way to limit the scope of Letters Patent granted hereon.

A liquid nutrient was prepared by thermophilic digestion in a 1000-gallon fibreglass fermenter. Alder chips having a size on the order of 0.5 inches by 0.25 inches by 0.03 inches were employed as the biodegradable material. The alder chips were combined with sufficient water to produce a 10% dry weight solids slurry. The slurry was aerated and agitated in accordance with the procedures outlined above without the addition of external heat. Thermophilic digestion temperatures in the range of 60° C. to 80° C. were experienced. Alder chips were also utilized as the supporting medium. The additional alder chips were introduced into the digester and allowed to ferment for one day after the original chips had digested at thermophilic temperatures for four days. After the additional alder chips absorbed liquid nutrient, they were screened from the digesting material and placed in 12"×18" trays that were 8 inches deep with an expanded metal bottom. The alder chips were placed in the trays to a depth of about seven inches. The bottom of the trays were positioned in a second larger tray to minimize evaporation while permitting adequate aeration for fungi growth.

The trays were spawned with *A. bisporus* and placed in a room maintained at 24° C. at a relative humidity of close to 100%. After two weeks, good mycelial growth was experienced. The trays were then cased with a 1:1 weight ratio mixture of peat and limestone. The casing material was placed on top of the growing medium to a depth of 1.0 inch. The trays were then placed in a room at which the temperature was maintained at 16° C. After about ten days numerous pinheads (small mushrooms) appeared in numerous clumps in all the trays. Mushrooms were harvested from the trays about ten days after the first pinheads emerged.

The alder chips in the trays were then copiously irrigated with additional cooled (16° C.) liquid nutrient from the digester. Sufficient amounts of liquid nutrients were contacted with the growing bed so that the alder chips were again saturated. The casing on the beds was renewed. The beds were then maintained at a temperature of 16° C. Pinheads were formed within four to five days. The pinheads developed normally into commercial-sized mushrooms for harvesting. A high relative humidity on the order of 90% was maintained during that period. The moisture in the beds was maintained by spraying with water every two to three days. Commercial-sized mushrooms were harvested from the trays for about the next three weeks.

The fungi-growing method of the present invention has several advantages over prior art methods. First, fungi can be grown without the application of conventional commercial sterilization of the liquid nutrient and/or the support medium. Previously, growing beds required steam heating or application of chemical sterilants such as ethylene oxide to fully sterilize the support medium and nutrient source. The thermophilic liquid nutrient produced as set forth above also provides protection for increased periods of time against adverse microorganism contamination that previously occurred when fungi were grown in covered or sealed fermentation vessels. Furthermore, the present invention provides a liquid nutrient for the growing of fungi, as opposed to the composted solid materials currently utilized to grow mushrooms, allowing the nutrient source to be replenished while the mushrooms are in the fruiting body growth stage. The present invention also does not require the removal of contaminants or undesirable microflora from the nutrient bed prior to inoculation with the desired fungi or other microorganism. Additionally, if it is desired to use straw as the support medium, spraying and recycling the hot thermophilic liquid over the straw breaks the waxy coating so that the nutrient absorbency is increased.

Accordingly the present invention does provide greater capability to reproducibly control nutrient values while providing fewer disease problems that might otherwise arise from pathogens, virus, and the like. The present invention also allows the production of uniform growing beds in which the liquid nutrient can be uniformly distributed. The continuous production system of the present invention also allows a harvesting cycle every ten days as opposed to only five flushes or harvests within a four-month period followed by disposal of the entire mushroom bed when prior art methods are employed. Because of the high nutrient content of the liquid nutrient, crop yields can be increased. And finally, the method can be utilized not only to produce edible mushrooms, but also to produce other types of mushroom and to grow mycelia for use in the pulp and paper industries and for animal feed.

The present invention has been described in relation to a preferred embodiment. It is to be understood that one of ordinary skill after reading the foregoing specification can effect various changes, substitutions of equivalents, and other alterations to the methods taught without departing from the broad concepts disclosed herein. It is therefore intended that the scope of Letters Patent granted hereon be limited only by the definition contained in the appended claims and equivalents thereof.

The embodiments of the invention in which an exclusive property or privilege is claimed are defined as follows:

1. A method for producing fungi comprising the steps of:
   providing a relatively inert support medium for physically supporting fungi growth,
   contacting said support medium with a liquid nutrient comprising the product of thermophilic, aerobic digestion of biodegradable organic material to provide a growing bed,
   inoculating the liquid nutrient with spawn without sterilization of said liquid nutrient,
   maintaining the liquid nutrient in said growing bed at a predetermined temperature and moisture content to promote the growth of mycelia.

2. The method of claim 1 further comprising the steps of:
   after the mycelia appear, casing the growing bed to promote the growth of fruiting fungi bodies.

3. The method of claim 1 wherein said fungi comprise mushrooms.

4. The method of claim 3 wherein said fungi is selected from Agaricus or Pleurotus.

5. The method of claim 1 wherein said liquid nutrient is contacted with spawn after said liquid nutrient is contacted with said support medium to form a growing bed.

6. The method of claim 1 wherein said liquid nutrient is first inoculated with spawn and thereafter contacted with said support medium to form said growing bed.

7. The method of claim 1 wherein said relatively inert support medium is porous and capable of absorbing said liquid nutrient.

8. The method of claim 1 wherein said growing bed is contacted with fresh liquid nutrient after a predetermined amount of the nutrient value thereof has been consumed.

9. The method of claim 1 wherein fresh liquid nutrient is supplied to said growing bed on a continuous basis.

* * * * *